United States Patent [19]
Snow

[11] Patent Number: 6,068,482
[45] Date of Patent: May 30, 2000

[54] METHOD FOR CREATION AND UTILIZATION OF INDIVIDUALIZED 3-DIMENSIONAL TEETH MODELS

[76] Inventor: Michael Desmond Snow, 39 Balcombe Rd., Mentone Victoria 3194, Australia

[21] Appl. No.: 09/233,685

[22] Filed: Jan. 19, 1999

Related U.S. Application Data

[63] Continuation of application No. 08/785,664, Jan. 17, 1997, abandoned.

[51] Int. Cl.[7] .................................................. A61C 5/10
[52] U.S. Cl. .......................... 433/223; 433/215; 433/24
[58] Field of Search ........................... 433/2, 8, 24, 223, 433/229

[56] References Cited

U.S. PATENT DOCUMENTS

| | | |
|---|---|---|
| 4,575,805 | 3/1986 | Moermann et al. . |
| 4,837,732 | 6/1989 | Brandestini et al. . |
| 5,273,429 | 12/1993 | Rekow et al. . |
| 5,372,502 | 12/1994 | Massen et al. . |
| 5,431,562 | 7/1995 | Andreiko et al. .......................... 433/24 |
| 5,518,397 | 5/1996 | Andreiko et al. .......................... 433/24 |
| 5,533,895 | 7/1996 | Andreiko et al. .......................... 433/24 |
| 5,549,476 | 8/1996 | Stern . |
| 5,569,578 | 10/1996 | Mushabac . |
| 5,879,158 | 3/1999 | Doyle et al. ............................... 433/24 |

OTHER PUBLICATIONS

Snow et al., "Interactive Computer Technologies in Dentistry", *Health Care in the Information Age*, H. Sieburg, S. Weghorst, and K. Morgan (Eds.), IOS Press and Ohmsha, 1996, pp. 411–421 (Chapt. 48).

*Primary Examiner*—Nicholas D. Lucchesi
*Attorney, Agent, or Firm*—Townsend Townsend & Crew LLP; Jim F. Hann, Esq.

[57] ABSTRACT

A computerized dental record method includes imaging a patient's teeth as a two-dimensional image, visually superimposing an initial three-dimensional computerized tooth model onto the two-dimensional image of the patient's teeth, interactively adjusting the three-dimensional teeth so that they are aligned with the two-dimensional image, and then storing the adjusted computer graphic model of the teeth as the dental record.

6 Claims, 4 Drawing Sheets

METHOD FOR CREATION AND UTILIZATION OF INDIVIDUALIZED 3-DIMENSIONAL TEETH MODELS

CROSS-REFERENCE TO RELATED APPLICATION

This application is a Continuation of U.S. patent application Ser. No. 08/785,664, filed Jan. 17, 1997, the disclosure of which is incorporated by reference.

FIELD OF THE INVENTION

The present invention relates to the field of dental anatomy and in particular, to storing and utilising 3D computer graphic structures representative of a patient's individual tooth and jaw structure.

BACKGROUND OF THE INVENTION

At present, dentists and orthodontists, when examining patients and keeping records of their teeth structure essentially operate substantially in a world of physical three and two dimensional records. Further, the present methods of operation are unduly cumbersome. A dentist or orthodontist, when planning a treatment for a patient, will generally manually produce a plaster mould which is a 3D representation of the patients teeth. In addition, X-ray images are also used to highlight other anatomical details. The production of these 3D moulds is generally cumbersome and further results in the requirement to store the moulds handy to the treatment location for future examination. Further, a like treatment of medical images such as X-rays is also required.

SUMMARY OF THE INVENTION

It is an object of the present invention to provide an alternative form of keeping and utilising dental patient records, and allowing for the interaction there between.

In accordance with the first aspect of the present invention there is provided a 3D computer graphic model of a set of teeth, each of the teeth being manipulable by an interactive manipulation means to accurately reflect the current position of a patient's set of teeth. Preferably, the placement of the teeth is derived from corresponding images of plaster cast and/or medical images of the teeth.

Further, the computer graphic model preferably has the ability to automatically produce a sequence of images mapping movements of teeth from a first position corresponding to the patient's current state to an idealised second position.

Further, the model preferably includes the ability to add brackets to the surfaces of any tooth and to simulate the likely movements of any or all teeth under the forces produced by the orthodontic appliances. Additionally, advantageously there is provided the ability to accurately model likely teeth and jaw movements when bands etc, are utilised in conjunction with the brackets to produce regionalised forces acting on tooth surfaces. The preferred system having full interactive ability to determine the extent of forces by means of direct user input. Further, an alternative form of the invention can include the ability to measure sensor inputs and to input the measured sensor inputs into the 3D graphical model for providing simulated jaw movements of the model. Further, simulated sound output is also preferably provided, simulating or rendering the recorded or likely sound to be heard when the teeth are brought into contact with one another (dental occlusion). In accordance with a second aspect of the present invention there is provided a method of automatically determining cephalometric structures in a cephalometric radiograph which can optionally include utilising the corresponding 3D computer graphic model as aforementioned to determine positions of cephalometric structures on an X-ray image. Preferably, the system allows for interactive alteration of any and all cephalometric structures and measures.

In accordance with a further aspect of the present invention there is provided a method of keeping patient dental records comprising:

(a) providing a 3D model of a standard set of teeth which is interactively manipulable by a user;

(b) utilising said model compostied over a medical image corresponding to a patient's dental structure by means of adjusting the tooth position within said model to match said medical image.

In accordance with a further aspect of the present invention there is provided a method of creating brackets and/or braces for orthodontic treatment comprising:

(a) determining an accurate individualised 3-dimensional computer graphical model of a patient's teeth;

(b) utilising said model to place at least one simulated bracket on the surface of at least one of said teeth;

(c) adapting said simulated bracket to the corresponding surface of said tooth; and (d) utilising said simulated bracket to produce a corresponding actual bracket for utilization in said orthodontic treatment.

BRIEF DESCRIPTION OF THE DRAWINGS

Notwithstanding any other forms which may fall within the scope of the present invention, preferred forms of the invention will now be described, by way of example only, with reference to the accompanying drawings in which.

DESCRIPTION OF PREFERRED AND OTHER EMBODIMENTS

In the preferred embodiment of the present invention, an individualised 3D model of a patient's teeth is created from two dimensional dataset representations and a standard 3D model utilising a computer system. The preferred embodiment can be implemented utilising a standard high end Pentium (trade mark) based personal computer system running a high end operating system such as "Windows NT(Trade Marks) and a 3D modelling language modelling, for example, the standard virtual reality mark-up language (VRML). Further, a high end standard Twain compatible scanner should be provided, inter-connected to the computer, for the scanning of images.

Figure 1:
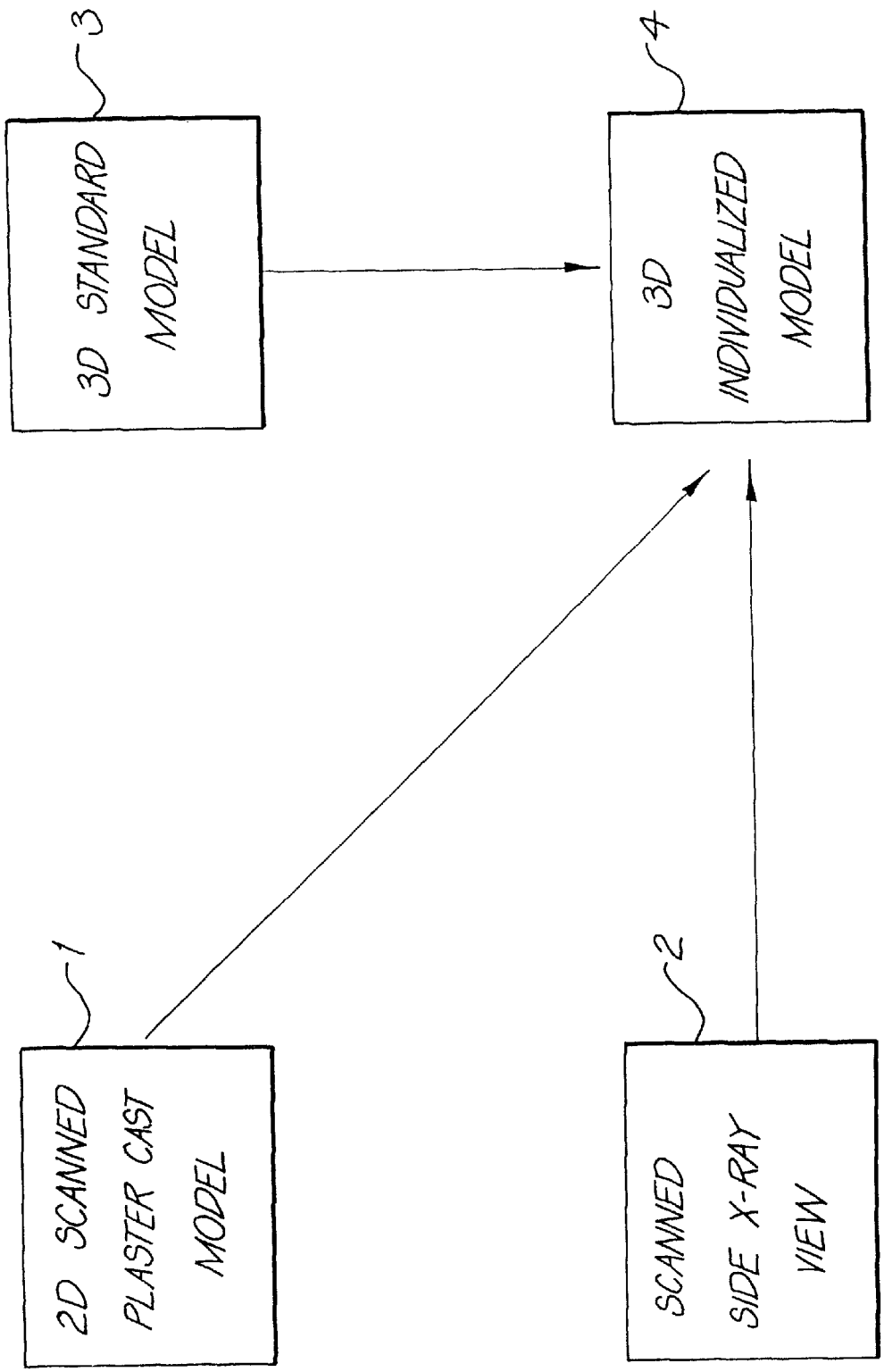
FIG. 1 illustrates the steps of a first form of creation of an individualised 3D model of a patient's tooth position.

Referring to FIG. 1, the usual 2D plaster cast model 1 taken from a patient is digitally rendered by placing it on a Twain compatible flat bed scanner or equivalent device to produce a scanned 2D image of both the upper and lower jaws. Further, the usual side medical images 2, such as X-rays, are also digitally rendered into the computer system by scanning.

A 3D "standard" model 3 for the patient is provided. The 3D standard model is represented by a three dimensional computer graphical representation of a standard male or female patient's teeth as required. It is well known in the field of dentistry that the structure of individual's teeth in respect of their size and shapes is substantially of low variance across a general population. However, there is a high variance generally with respect to position or placement of an individual's teeth. Hence, the use of the standard 3D models is well known in clinical teaching and in practice. The 3D standard model can be created in a 3D computer graphical form as a "once off" by laser scanning a physical example of the corresponding 3D standard model or by other known techniques for entering 3-dimensional data into a computer system.

Figure 2:
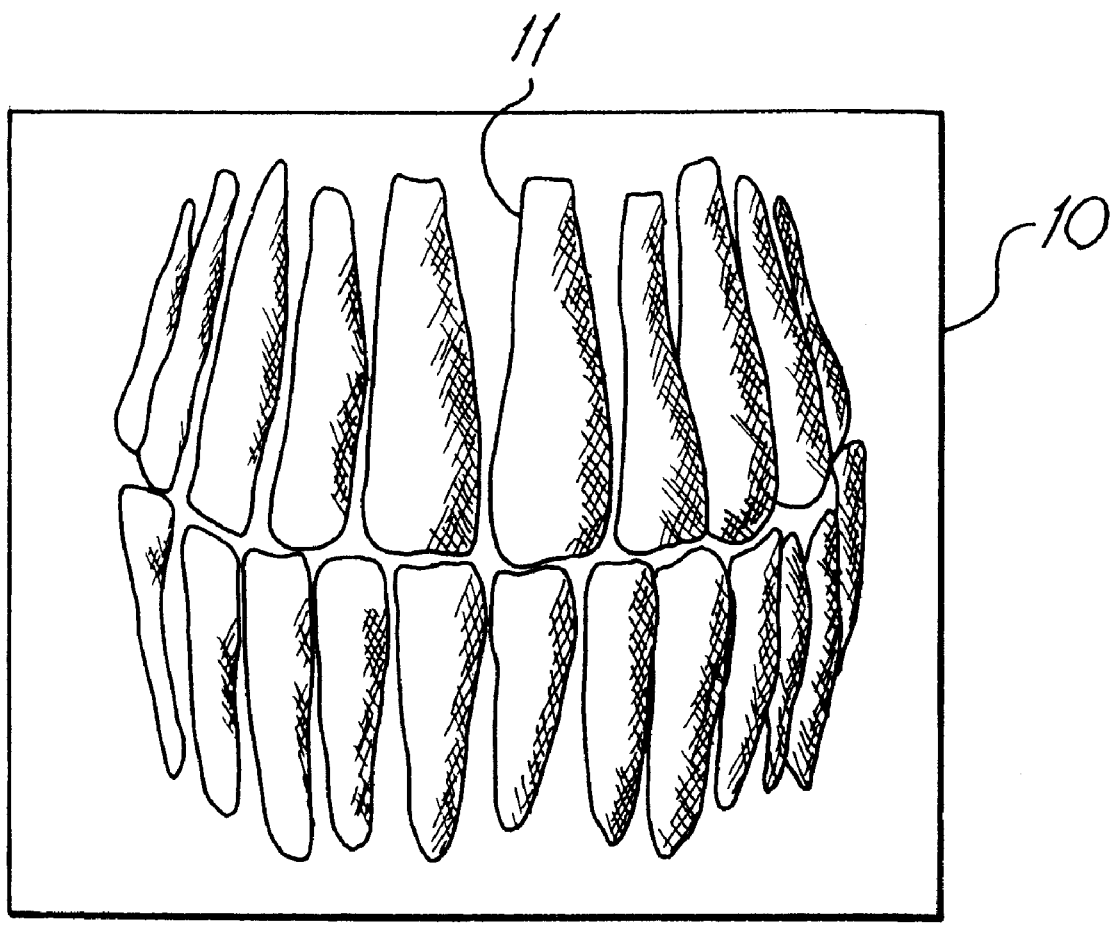
FIG. 2 illustrates an example standard 3D tooth model.
Figure 3:
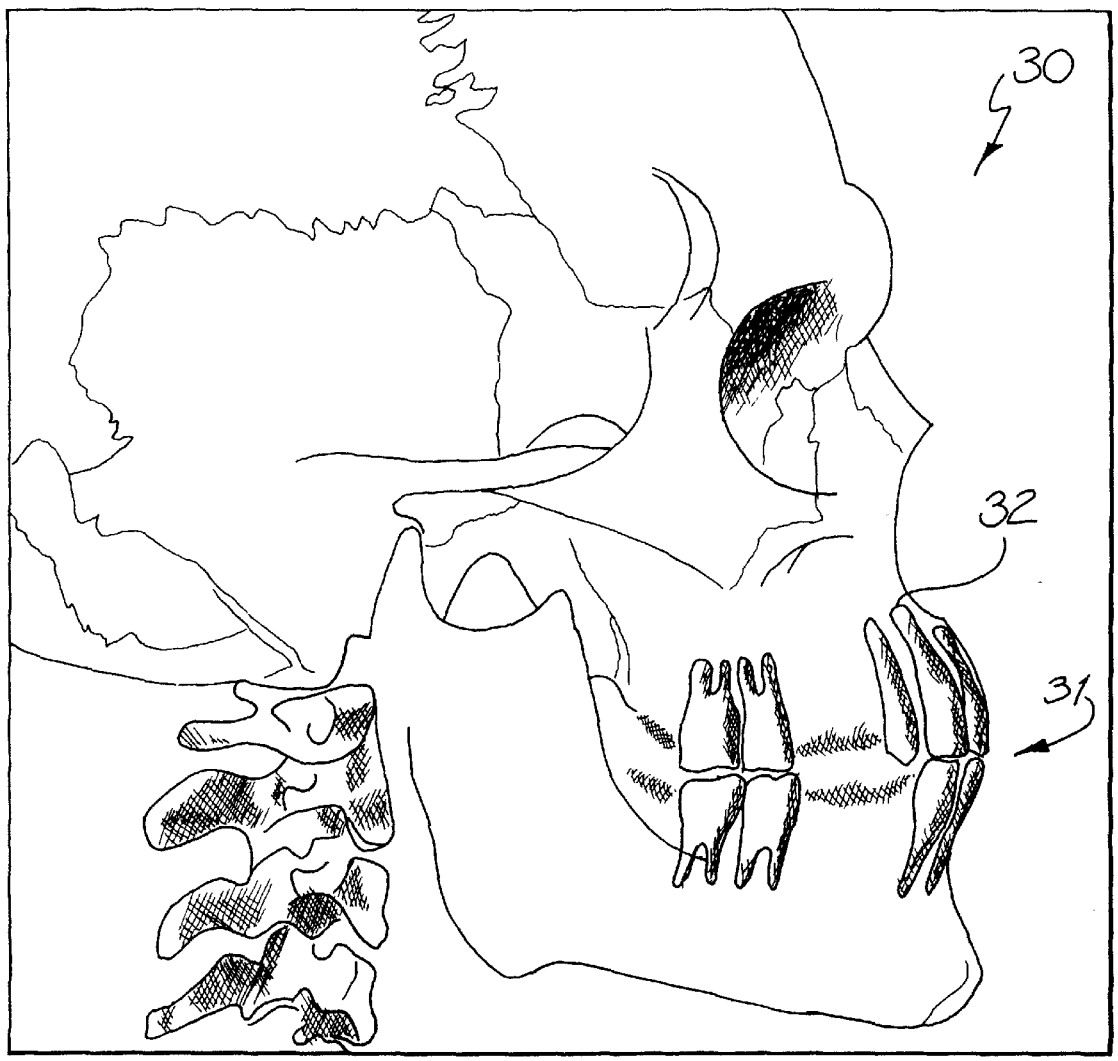
FIG. 3 illustrates the process of manipulation of the standard model in front of a corresponding X-ray image to derive a patient model for the tooth positions.

Turning now to FIG. 2, there is illustrated an example 10 of the three dimensional computerised form of the standard teeth model. Preferably, the 3D form includes the usual controls (not shown) for the location, scaling and translation of each of the upper and lower jaws. Also, preferably, controls are included for the scaling translation and rotation of each tooth 11 independently. Further, each tooth 11 can preferably be selected to be visible or invisible in accordance with a particular patient's jaw profile. Further, each tooth 11 can be made partially transparent. Further standard enhancements, such as the placement of computer graphical lighting sources to provide shading and other 3D enhanced effects which normally are of standard 3D modelling packages can also be utilized for enhanced realism.

Turning again to FIG. 1, in the preferred embodiment, the 3D standard model 3 is utilised, in conjunction with the "scanned" plaster cast model 1 and/or a profile X-ray view 2, to produce a 3D individualised model 4 which differs from the standard 3D model 3 in a patient specific manner. The individualised 3D model can then be utilised as a patient record for treatment planning and record keeping.

Figure 4:
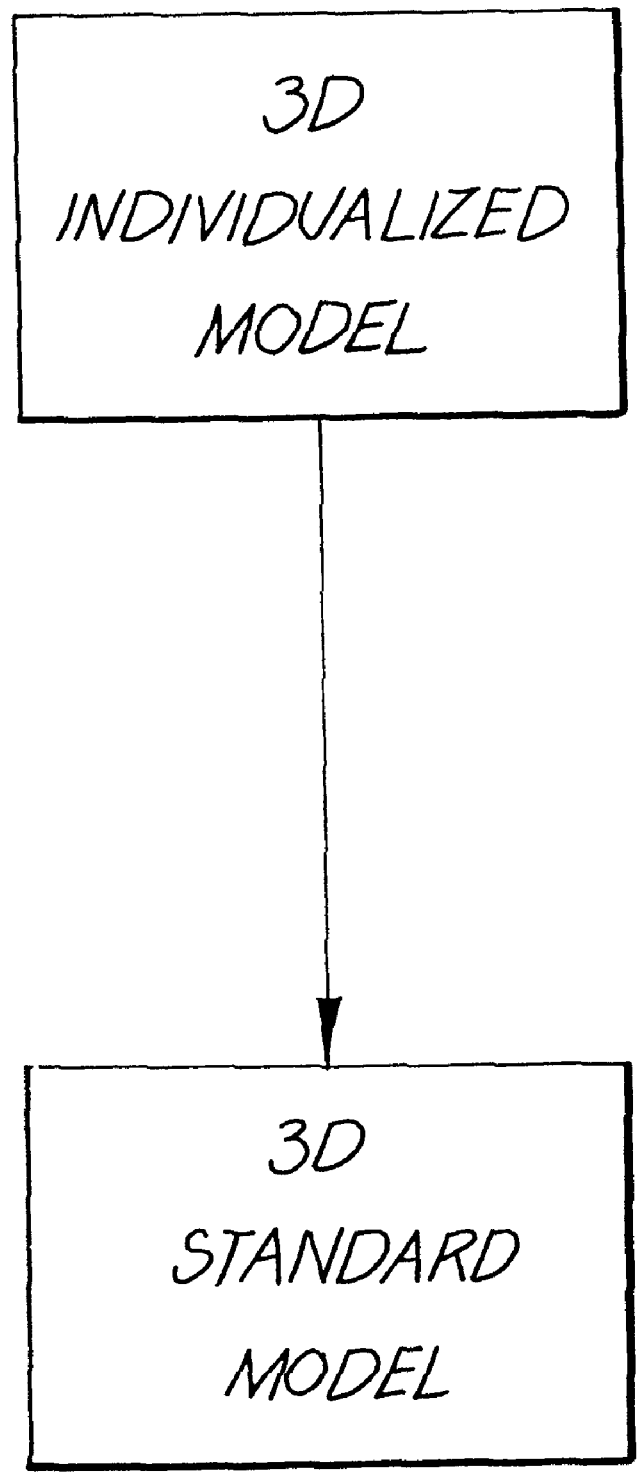
FIG. 4 illustrates a process for interpolation between a 3D individualised model and a 3D standard model.

The 3D individualised model can be determined from the standard model by many different techniques known to those skilled in the art of computer graphics and image processing. One form of manual orientation of teeth position will now be illustrated with reference to FIG. 4. In this case, the patient's X-ray image 30 is displayed on the computer screen as a background image for the 3D standard model. The standard model is then rotated, translated and scaled by the user so as to match the orientation of the X-ray image 30. The individual teeth eg. 32 are then adjusted by means of translation, scaling and rotation so as to match the X-ray image. Preferably, each tooth can be made partially transparent so as to enhance the alignment of the tooth 32 with the X-ray image.

A similar process can then be carried out utilising the two dimensional scanned cast model. The cast model can be scanned in and displayed as a background image. The three dimensional computer graphic model can be overlaid over the cast model in jaw alignment, in a partially transparent form and each individual tooth adjusted so as to correctly place it relative to the cast model. Preferably, this process can be carried out for each individual upper and lower jaw separately with the other jaw being "turned off" via a suitable user interface and the tooth adjustments made. Although the aforementioned method of adjustment of the standard tooth model requires manual intervention by the experienced user, the utilisation of tooth models having a degree of transparency results in an accurate positioning of the computer graphic model relative to a patient's actual teeth position.

Upon optimisation of the 3D individualised model, to teeth positions corresponding to those of the individual patient, these are then saved and utilised as a computerised form of record for that patient.

Other forms of fusion of the 2D moulds are possible and such techniques will be known to those skilled in the art of image analysis and 3D graphics. This further includes turning off individual teeth as required.

In a further refinement, the 3D individualised model can be utilised in treatment planning to produce an improved form of treatment planning. It is often the objective in orthodontic treatment to overcome individual anomalies in an individual patient's arrangement of teeth. Hence, in a further refinement, referring to FIG. 4, the position of an individual's teeth is first measured and reflected in the 3D model, utilizing the aforementioned techniques. The location and rotation of each tooth in the individualized 3D tooth model relative to the standard model is then noted. Next, a mapping from the position of each individual tooth in the 3D individualised model 4 to the corresponding position of the tooth in the 3D standard model 3 is determined by means of a series of interpolation steps between the two models, with the distance between interpolation steps being preferably a user defined parameter.

The computer system is then programmed to "animate" the movement of teeth from the 3D individualised model 4 to the 3D standard model through the series of steps from one model to the next model, rendering each step in turn for the specialist or patient to view.

In a further refinement, utilizing the 3D computer model, accurate position sensors can be utilized to a patient's upper and/or lower jaws. The position sensors can be utilized to accurately track movement of the patient's lower jaw in opening and closing of the patient's mouth to define a motion of the lower jaw with respect to the upper jaw. This data can then be utilized for movement of the two jaws, one relative to the other. In the 3D computer graphic model, each jaw is treated separately and the lower jaw is then programmed to move relative to the upper jaw in accordance with the pathway defined by the position sensors. Accurate jaw movement tracking gives the orthodontist the ability to accurately view a patient's likely jaw movement for each corresponding movement in individual tooth arrangements thereby locating likely problems in a patient's treatment program.

In a next refinement of the preferred embodiment, a simulation of the sound of the 3D computer graphic model of the two animated jaws being drawn together is created or recorded. Although many refinements are possible, in one form, the total surface area likely to make contact between surfaces of the two jaws when brought together is calculated and an audible sound, having frequency components preferably substantially inverse to the amount of surface area being brought together is produced to simulate a corresponding actual sound. It will be understood by the expert in computer graphics that a certain degree of variation on the present theme is possible. For example, the definition of contact can be extended to a certain degree of proximity of two surfaces with an assumed degree of "play" in the surfaces being connected. Further, more accurate models are envisaged whereby a fourier analysis of actual teeth clenching is conducted and measurements made of the likely degree of contact and the profile of contact of two surfaces and the sound produced for those degrees of contact. Of course, other refinements are possible, including exaggeration of the likely sounds in order to assist the orthodontist in profiling the actual contact being made by any particular patient. Indeed, many different alterative sound formats could be provided simultaneously with a selection being under the control of a specialist user via the usual graphical user interface.

In a further refinement of the preferred embodiment, a means can be provided for conducting automated cephalometric analysis of the 2D X-ray image of the patient. In a first refinement, the computer graphics means can be utilised for display of X-ray images with various sets of cephalometric data points displayed over the X-ray image for individual manipulation by a user of the system. The overlays can include points of interest, connected lines, splines and other curves, which can be collectively manipulated to conduct various analyses such as Bjork, Boulton's Triangle, Downs, Down Harold McNamara, Ricketts, Sterner, Tweed, Wits and Wylie cephalometric analysis. Preferably, a collection of expected landmarks for adjustment by the orthodontist is initially provided in accordance with any of the above alternative analyses. Upon selection of the desired treatment, a specialist user is able to manipulate each individual line, spline or points placed over an X-ray image structure of the patient and thereby adjust the example set of lines to customise the results of the chosen analysis. The customised analysis is preferably able to be stored and retrieved as required, with each analysis being able to be dynamically altered as required.

In a further refinement, the individualized customization of the points, curves and lines are automatically derived from the X-ray image utilising the patient's corresponding 3D model. It will be readily evident that the cephalometric analysis can be automatically conducted in a number of different ways, including directly locating the cephalometric points in the X-ray image. Alternatively, the 3D individualised model as derived in accordance with the principles aforementioned can be utilised to locate the cephalometric points and then mapped to the relevant X-ray image as located from the X-ray image of the same individual.

In a further refinement and use of the preferred embodiment, the personalised 3D computer graphic model can be utilised for the placement of brackets and/or braces thereupon. Different suitable brackets can initially be created. The chosen bracket can be individually located interactively on the 3D model with the bracket's size, shape and position being adjusted by the expert orthodontist. Upon determination of a final position of brackets, the bracket can be individually structured to contour a corresponding surface of the tooth so as to minimise stress variance across the tooth or to minimise the possible damage to the tooth as a result of placement of each bracket but providing a better fit on the tooth surface. The individualised 3D model can then be utilised to create an individualised bracket with accurate measurements with the surface of each bracket accurately profiled to match the corresponding surface in the individualised tooth. The bracket structure can be output in a standard stereo lithographic format (STL) and later used to create a corresponding customized brackets/braces.

In a further refinement, the 3D computer graphic model and corresponding brackets can further include bracing rods etc, each having variable tensions and forces and the 3D model utilised to accurately project the movement of each tooth under the expected structural load. Means can then be provided for variation in the tension of braces, bands etc, and, through interactive feedback, the expert user can determine an individualised orthodontic treatment for the utilisation by a particular user.

It will be obvious to those skilled image processing and three dimensional computer graphics that many variations of the aforementioned embodiments are possible utilising the latest in three dimensional computer graphics techniques. Further, it would be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

What is claimed is:

1. A method of determining a dental record of a dental patient's teeth in a computer system comprising the steps of:

(a) imaging a patient's teeth so as to produce at least one two dimensional image of the patient's teeth;

(b) visually superimposing an initial 3-dimensional computer graphic model of a set of teeth having independently manipulable teeth objects onto said two dimensional image;

(c) interactively adjusting at least one of the position, orientation or scaled size of said manipulable teeth objects so that they are aligned with said two dimensional image; and (d) storing the adjusted computer graphic model of said set of teeth as said dental record.

2. A method as claimed in claim 1 wherein said two dimensional image comprises an X-ray image of said patient's teeth.

3. A method as claimed in claim 1 wherein said two dimensional image comprises a scanned image of a three dimensional impression made of a patient's teeth.

4. A method as claimed in claim 1 wherein said 3-dimensional computer graphic model includes an adjustable degree of transparency and said step (c) further includes adjusting the degree of transparency of at least one of said manipulable teeth objects.

5. A method as claimed in claim 1 further including the step of:

(e) utilizing said dental record as an initial state in an iteractive series of states having different orientations or positions of said manipulable teeth objects.

6. A method as claimed in claim 1 wherein said iteractive series of states include an initial state and a final state and wherein the series of states between the initial and final states are automatically generated.

* * * * *